United States Patent

Sparks et al.

[11] Patent Number: 5,964,800
[45] Date of Patent: *Oct. 12, 1999

[54] METHODS FOR ROTATING A PROSTHETIC HEART VALVE WITHIN A SEWING RING

[75] Inventors: Robert Sparks, Austin, Tex.; Chris Kingsbury, Laguna Hills; David Wieting, Costa Mesa, both of Calif.

[73] Assignee: Baxter International, Inc., Deerfield, Ill.

[*] Notice: This patent is subject to a terminal disclaimer.

[21] Appl. No.: 08/912,021

[22] Filed: Aug. 15, 1997

Related U.S. Application Data

[63] Continuation of application No. 08/376,624, Jan. 23, 1995, Pat. No. 5,716,398, which is a continuation of application No. 07/157,037, Feb. 16, 1988, abandoned.

[51] Int. Cl.[6] ........................................................ A61F 2/24
[52] U.S. Cl. .................................................................. 623/2
[58] Field of Search ........................ 623/2; 606/1; 81/436, 81/121.1

[56] References Cited

U.S. PATENT DOCUMENTS

| | | |
|---|---|---|
| 1,447,564 | 3/1923 | Norlund et al. . |
| 2,813,450 | 11/1957 | Dzus . |
| 3,400,626 | 9/1968 | Bergere . |
| 3,409,013 | 11/1968 | Berry . |
| 3,587,115 | 6/1971 | Shiley . |
| 3,628,535 | 12/1971 | Ostrowsky et al. . |
| 3,828,787 | 8/1974 | Anderson et al. . |
| 4,237,754 | 12/1980 | Battrick . |
| 4,655,218 | 4/1987 | Kulik et al. . |
| 4,679,556 | 7/1987 | Lubock et al. . |
| 4,683,883 | 8/1987 | Martin . |
| 4,702,250 | 10/1987 | Ovil et al. . |

FOREIGN PATENT DOCUMENTS 2 697 193  4/1994  France .

*Primary Examiner*—David H. Willse
*Attorney, Agent, or Firm*—Guy L. Cumberbatch; Debra D. Condino

[57] ABSTRACT

Methods for rotating a heart valve body rotatably mounted within a sewing ring. The valve body includes a plurality of drive surfaces on an inner periphery, and a rotator has a plurality of drive surfaces on an exterior periphery. The drive and driven surfaces are in registration only in discrete relative orientations of the two parts about a common axis of rotation. The drive surfaces may be greater in number than the driven surfaces, to reduce the rotational angle that the rotator must be turned before registering with the valve body. The drive and driven surfaces may be formed as flats on each respective part. In one embodiment, the rotator includes a cylindrical distal end with three pairs of diametrically opposed external flats, and the valve body includes a single pair of diametrically opposed internal flats. The rotator is designed so that a surgeon need only rotate it a maximum of 90° in either direction.

31 Claims, 2 Drawing Sheets

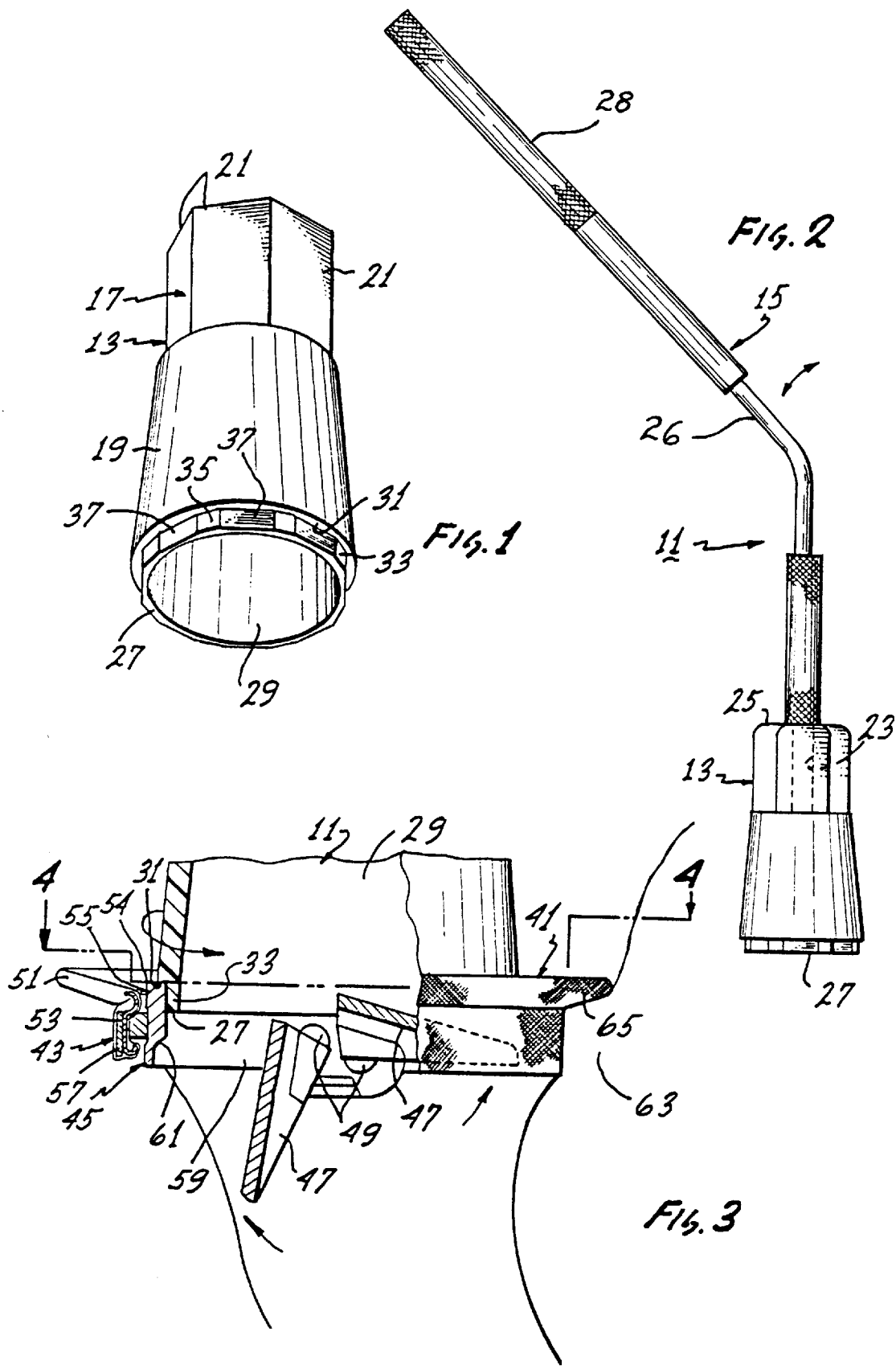

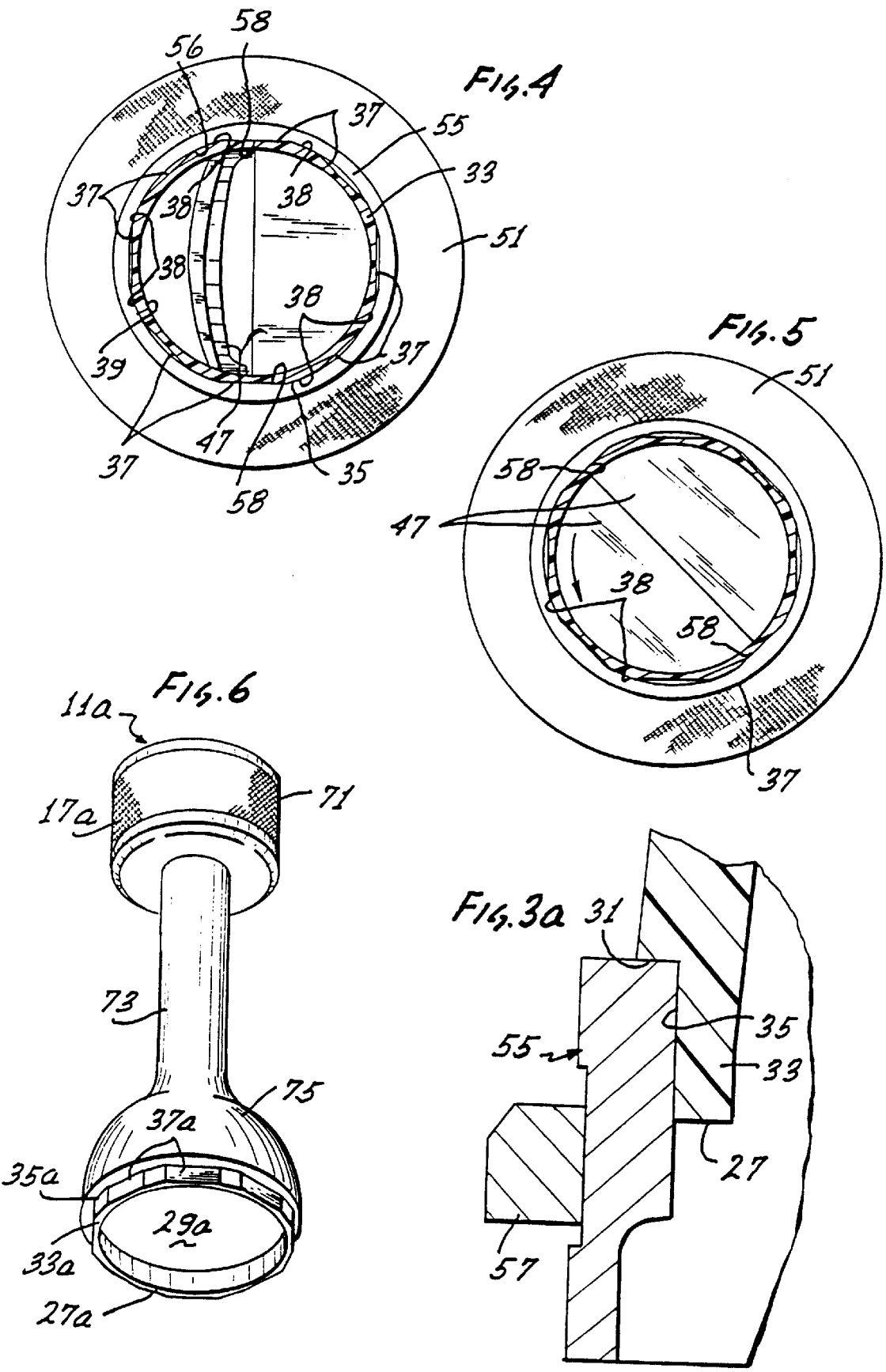

METHODS FOR ROTATING A PROSTHETIC HEART VALVE WITHIN A SEWING RING

This is a continuation of application Ser. No. 08/376,624, filed on Jan. 23, 1995, now U.S. Pat. No. 5,716,398, which is a continuation of application Ser. No. 07/157,037, filed on Feb. 16, 1988, now abandoned.

BACKGROUND OF THE INVENTION

As is well known, prosthetic heart valves are used as replacements for diseased natural heart valves. Generally, prosthetic heart valves are divided into two classes, i.e. mechanical valves and tissue valves. One form of mechanical valve employs two leaflets or, more broadly, valve elements, which pivot between open and closed positions. One problem with valves of this type is that the pivotal movement of the valve elements can be impeded by tissue near the orifice in which the valve is implanted.

One way to solve this problem is to employ a rotatable heart valve. A rotatable heart valve includes a frame attachable to tissue around the orifice, a rotor mounted on the frame for rotation and one or more valve elements carried by the rotor and movable with respect to the rotor to open and close the heart valve. The frame includes a suture ring, and to implant a valve of this type, the surgeon sutures the suture ring in the desired position within the heart. Next, the valve elements are manipulated to ascertain if their movement is impeded in any way. If movement of the valve elements is impeded, the surgeon rotates the rotor with respect to the frame to a new angular position in which the adjacent tissue does not impede the pivotal movement of the valve elements.

This technique is very satisfactory in reducing the likelihood that tissue will impede the pivotal movement of the valve elements. However, some difficulty has been encountered with the implement used to rotate the rotatable valve. For example, the implement disclosed in Martin U.S. Pat. No. 4,683,883 is designed to function as both a valve holder and valve rotator. Although satisfactory for some desired to drivingly engage the rotator with the rotatable valve particularly when the surgeon is working in regions not readily visible or at difficult angles. Furthermore, once the rotator does drivingly engage the heart valve, it is not as easy as desired to maintain this engagement during rotation of the valve. These factors are significant because it is important that the valve be rotated quickly and accurately to minimize the time required for this portion of the surgery and to assure accurate rotational positioning of the valve. In addition, in order to maintain the engagement desired, additional force may be applied to the rotator and hence to the heart valve, and this is also undesirable. Finally, some prior art valve rotators interfere with the pivotal movement of the valve elements, and this is undesirable because it inhibits the testing of the valve elements to assure that they can move freely between the closed and fully opened positions.

SUMMARY OF THE INVENTION

This invention provides a heart valve rotator which generally overcomes the disadvantages noted above. The rotator of this invention can be easily drivingly coupled to the rotatable valve and the driving engagement is easy to maintain with a minimum of force applied to the heart valve. Also, the valve rotator of this invention does not impede the free pivotal movement of the valve elements between the closed and fully open positions. Although this invention is particularly adapted for a mitral valve, it is also applicable to rotatable heart valves in general.

This invention can advantageously be embodied in a valve rotator which includes a body having a generally annular peripheral surface at one end of the body and a central cavity opening at such one end. The annular peripheral surface substantially surrounds the central cavity and faces outwardly. The annular peripheral surface has an interlocking surface region configured to interlock with a rotor of a rotatable valve. The body has a generally annular shoulder adjacent and generally facing such one end of the body. The annular peripheral surface extends toward such one end of the body from the annular shoulder.

Several factors contribute to the ease of drivingly coupling the valve rotator to the heart valve. For example, preferably, although not necessarily, the interlocking surface region includes a plurality of pairs of flat surfaces. By providing a plurality of pairs of flat surfaces, obtaining driving engagement is made much easier because less relative rotation between the rotator and heart valve is needed to obtain driving engagement.

Preferably, although not necessarily, the end of the body inserted into the heart valve is annular. This annular end of the body rides on the heart valve prior to driving engagement of the interlocking surface region of the body and the heart valve. Because this end is annular, it can more stably support the rotator than if one or more long lengths of this annular surface were removed.

Various features contribute to keeping the valve rotator drivingly coupled to the heart valve. For example, the annular peripheral surface and the annular shoulder stably support the rotator against rocking motion when the rotator is drivingly coupled to the heart valve. In addition, this enables the rotator and heart valve to stay engaged with less axial force applied to the heart valve.

To the extent that the pairs of flat surfaces are increased, obtaining driving engagement with the heart valve is made easier as described above. However, the flat surfaces, which are not in driving engagement with corresponding flat surfaces of the heart valve, are spaced from the heart valve where they are less able to offer stability to the driving connection between the rotator and the heart valve. However, this invention utilizes intermediate arcuate surfaces for spacing the flat surfaces circumferentially, and these intermediate arcuate surfaces are in continuous sliding engagement with the heart valve when the rotor is drivingly coupled to the heart valve. Preferably, the intermediate arcuate surface are contiguous adjacent flat surfaces so that the entire circumferential length of the annular surface is utilized either to facilitate initial driving engagement or to maintain such driving engagement.

A region of the body is insertable into the heart valve and the cavity is sized and positioned to prevent this region of the body from interfering with the free pivotal movement of the valve elements. In addition, means is provided for limiting the depth of insertion of this region of the body into the heart valve. This limiting means and the cavity prevent the body from interfering with movement of the valve element.

The cavity in the body can be arranged so that a portion of the valve element extends into the cavity in at least one position of the valve element. In a preferred construction, the heart valve includes a valve seat and the valve element is engageable with the valve seat to close the heart valve. The limiting means prevents such region of the body from extending into the heart valve all the way to the valve seat. The annular wall can have a variety of different shapes in radial cross section, such as cylindrical with one or more flats to form the interlocking surface region, polygonal, etc. Although the annular wall may have some interruptions, it should not have interruptions of sufficiently great circumferential length so as to materially diminish the firm seating engagement which a continuous annular wall would provide. Thus, in a preferred construction, the annular wall extends continuously around the cavity.

In a preferred construction, the body has an annular wall and the annular peripheral surface is on the annular wall. In this preferred construction, the cavity is at least partially defined by the annular wall.

The valve rotator can be manually rotated, and for this purpose, it is preferred to provide means at the other end of the body for facilitating manual gripping and rotating of the body. In addition, means is also provided at the other end of the body for attaching a handle to the body. The body can be simply and inexpensively manufactured by molding it from a suitable rigid plastic material.

The invention, together with additional features and advantages thereof, may best be understood by reference to the following description taken in connection with the accompanying illustrative drawing.

BRIEF DESCRIPTION OF THE DRAWINGS

FIG. 1 is an isometric view of one preferred form of heart valve rotator constructed in accordance with the teachings of this invention.

FIG. 2 is a side elevational view of a rotator which includes a handle.

FIG. 3 is a fragmentary elevational view partially in section showing the rotator and a rotatable heart valve.

FIG. 3A is an enlarged fragmentary sectional view of a portion of FIG. 3.

FIG. 4 is a sectional view taken generally along line 4—4 of FIG. 3.

FIG. 5 is a sectional view similar to FIG. 4 with the rotor of the heart valve rotated by the rotator and with the valve elements closed.

FIG. 6 is an isometric view of a second form of heart valve rotator constructed in accordance with the teachings of this invention.

DESCRIPTION OF THE PREFERRED EMBODIMENT

FIG. 2 shows a heart valve rotator 11 which comprises a body 13 and an optional handle 15. The body 13 is preferably integrally molded of a suitable rigid plastic material.

In this embodiment, the body 13 includes a coupling section 17 and a generally frusto-conical skirt 19. The coupling section 17 has means for facilitating manually gripping and rotating of the body 13, and in this embodiment, such means is in the form of a plurality of flat surfaces 21. Six of the flat surfaces 21 are illustrated, and the coupling section 17 is hexagonal, but this is purely illustrative. The coupling section 17 also has an internally threaded axial bore 23 (FIG. 2) extending completely through it. The threads cooperate with mating threads of the handle 15 to releasably attach the handle to the body 13. The coupling section 17 also defines a proximal end 25 of the body.

The handle 15 is an elongated metal handle with a thin bendable section 26 and a knurled grasping section 28. The handle 15 may be conventional and of the type used with a heart valve holder to insert the heart valve into the heart for implantation.

The skirt 19 defines an annular distal end 27 of the body 13 and cooperates with the coupling section 17 to define a central cavity 29 which opens at the distal end. In this embodiment, the distal end 27 is a planar surface which lies in a radial plane and which is continuous and uninterrupted.

The skirt 19 has an annular shoulder 31 (FIG. 3A) adjacent the distal end 27. The annular shoulder 31 is a planar surface and lies in a radial plane so that it faces the distal end 27. A distal region of the skirt 19 forms an annular wall 33, which partially defines the cavity 29 and which extends from the annular shoulder 31 to the distal end 29. The annular wall 33 has an annular peripheral surface 35 which faces radially outwardly and which has an interlocking surface region in the form of a plurality of pairs of flat surfaces 37 (FIG. 4). Although four pairs of diametrically opposed flat surfaces 37 are illustrated, this is purely illustrative. Adjacent flat surfaces 37 are spaced circumferentially by intermediate arcuate surfaces 38 which are contiguous with the flat surfaces.

The annular wall 33 extends continuously and without interruption around the cavity 29. As best seen in FIG. 4, the annular wall 33 has an inner surface 39 which is circular in radial cross section and which is slightly conical. The annular peripheral surface 35 is generally cylindrical except for the presence of the flat surfaces 37.

The rotator 11 is particularly adapted for use with a rotatable heart valve, such as rotatable mitral heart valve 41. The heart valve 41, which may be of conventional construction, comprises an annular frame 43, an annular rotor 45 and a pair of valve leaflets or valve elements 47 pivotally attached to the rotor 45 in a conventional manner, such as by mounting balls 49 carried by the valve elements and pivotally received in the rotor 45. The frame 43 can be of any conventional construction for a rotatable heart valve, and as such, may include a suture ring 51 and a relatively rigid mounting ring 53. The rotor 45 may comprise, for example, a housing 55 of annular construction and a stiffener ring 57 surrounding the housing and fixedly attached thereto. The stiffener ring 57 is receivable in a corresponding annular groove in the mounting ring 53 to mount the rotor 45 for rotation relative to the frame 43. Rotational movement of the rotor, relative to the frame 43 is retarded by frictional forces which are sufficient to retain the rotor in whatever angular position it is placed. The housing has an upper end or flat annular shoulder 54 lying in a radial plane and an inner generally circular surface 56 as viewed in cross section (FIG. 4) with one pair of diametrically opposed flat driven surfaces 58.

The rotor 45 has an opening 59 extending therethrough in which the valve elements 47 are pivotally mounted. The valve elements can be pivoted between a closed position illustrated by the right-hand valve elements 47 in FIG. 3 and an open position illustrated by the left-hand valve element in FIG. 3. Of course, in actual use, the valve elements 47 will open and close together and the position of the valve elements 47 in FIG. 3 is for illustrative purposes only. The housing 55 has an annular valve seat 61 which is engaged by the periphery of the valve elements 47 in the closed position of the valve 41. The heart valve 41 illustrated and described herein is commercially available from Baxter of Irvine, Calif., and for that reason, is not described in greater detail herein.

In open-heart surgery, the diseased natural valve is removed and the prosthetic heart valve 41 is implanted by suturing the suture ring 51 to tissue 63 surrounding the orifice 65 in which the heart valve 41 is placed. This is accomplished according to conventional techniques with the surgeon roughly angularly orienting the heart valve 41 to achieve the approximate desired angular orientation of the valve elements 47 about the axis of the orifice 65 before the heart valve 41 is sutured in place. After the suture ring 51 is sutured to the tissue 63, the surgeon manipulates the valve elements 47 between the closed and fully open positions to ascertain if any of the tissue 63 adjacent the valve is impeding the free pivotal movement of the valve element. If such impediment exists, the surgeon rotates the rotor 45 and the valve leaflets 47 to a new angular position in which there is no impediment to the free pivotal movement of the valve element.

To accomplish this, the surgeon inserts the annular wall 33 into the opening defined by the inner surface 56 of the housing 55 of the rotor 45. This insertion process is facilitated by the presence of multiple pairs of the flat surfaces 37. Accordingly, regardless of the angular position of the rotator 11 when it first contacts the shoulder 54 of the housing 55, only a relatively small amount of rotation of the rotator is necessary to align one pair of the flat surfaces 37 with the flat driven surfaces 58 of the housing 55 of the rotor 45. In addition, this short degree of rotation can be more stably carried out because the distal end 27 is a continuous, flat annular surface which is better able to support the rotator on the shoulder 54 during this rotational movement.

Once the annular wall 33 is received within the housing 55 as shown in FIGS. 3 and 3A and driving engagement between the flat surfaces 37 and 58 is achieved, it is relatively easy to keep the valve rotator 11 drivingly coupled to the rotor 45. In this regard, the annular peripheral surface 35 provides firm seating engagement with the inner surface 56 of the frame 55 to stably support the rotator against rocking motion. This also enables the rotator 11 and the rotor 45 to stay drivingly engaged with less axial force applied to the heart valve 41. The rotator 11 can be manipulated and rotated by grasping the flat surfaces 21 or by using the handle 15.

Although the flat surfaces 37, which are not drivingly engaged with the driven surfaces 58 are not in continuous contact with the inner surface 56, the intermediate surfaces 38 provide such continuous contact and the non-engaged flat surfaces 37 are closely adjacent the inner surface 56. Accordingly, this arrangement of multiple sets of flat surfaces 37 and intermediate surfaces 38 provides for a desired combination of establishing driving engagement and for maintaining such driving engagement.

With the rotator 11 seated in the rotor 45 as shown, the shoulders 31 and 54 engage to limit the depth of insertion of the annular wall 33 and the distal end 27 into the rotor 45. Specifically, the distal end 27 does not extend to the valve seat 61 where it could interfere with complete movement of the valve elements 47 to the closed position.

Also, the cavity 29 helps prevent the body 13 from interfering with movement of the valve elements 47 with respect to the rotor 45. In this regard, the cavity 29 provides space into which portions of the valve elements 47 can extend as shown in FIG. 3.

FIG. 6 shows a heart valve rotator 11a which is identical to the heart valve rotator 11 in all respects not shown or described herein. Portions of the heart valve rotator 11a corresponding to portions of the heart valve rotator 11 are designated by corresponding reference numerals followed by the letter a.

The coupling section 17a differs from the coupling section 17 in that it has an annular knurled region 71 in lieu of the flat surfaces 21 to facilitate manual gripping. In addition, the coupling section 17a is generally cylindrical and does not have means for attaching of the handle 15.

The rotator 11 has a solid plastic stem 73 of reduced diameter which joins the coupling section 17a to a generally dome-shaped head 75. The cavity 29a is relatively shallow and is formed in the head 75. Thus, the rotator 11a effectively eliminates the skirt 19 in favor of the stem 73 and the head 75 and any skirt in the rotator 11a is quite short and limited to the depth of the cavity 29a.

Although exemplary embodiments of the invention have been shown and described, many changes, modifications and substitutions may be made by one having ordinary skill in the art without necessarily departing from the spirit and scope of this invention.

We claim:

1. A method of implanting and adjusting a heart valve in an orifice of a human heart, comprising:

providing a heart valve having an outer sewing ring and an inner rotor with an inner surface having a pair of diametrically opposed driven surfaces, the rotor being rotatable with respect to the sewing ring and having a pair of leaflets pivotally mounted within the inner surface;

positioning the heart valve adjacent the orifice;

suturing the sewing ring to the orifice;

providing a valve rotator having a proximal handle attached to a distal body, the body terminating in an annular peripheral surface defining a central axis and a plurality of discrete drive surfaces adapted to engage the driven surfaces on the rotor and couple rotation of the rotator and rotor;

positioning the rotator distal body adjacent the heart valve rotor in a first orientation with the central axis aligned with the rotor axis of rotation;

rotating the rotator from the first orientation less than 90° about the central axis in either direction and axially advancing the rotator to engage the drive surfaces and the driven surfaces, the drive surfaces and driven surfaces being respectively configured to cooperate and preclude the need to rotate the rotator by 90° or more in either or both directions before the rotator can be axially advanced; and rotating the rotor within the sewing ring.

2. The method of claim 1, wherein the drive surfaces comprise outwardly facing flats interrupting the annular peripheral surface, and the driven surfaces comprise flats formed on the inner rotor surface.

3. The method of claim 2, wherein there are at least three pairs of diametrically opposed flats formed on the annular peripheral surface, and the driven surfaces comprise a single pair of diametrically opposed flats.

4. The method of claim 1, further including disengaging the rotator and the rotor by axially withdrawing the rotator without any further manipulation thereof.

5. The method of claim 1, wherein there are more than one pair of diametrically opposed drive surfaces on the rotator, and a single pair of diametrically opposed driven surfaces on the rotor.

6. The method of claim 1, wherein the step of rotating the rotator from the first orientation comprises rotating the rotator less than 60° about the central axis in either direction, the drive surfaces and driven surfaces being respectively configured to cooperate and preclude the need to rotate the rotator by 60° or more in either or both directions before the rotator can be axially advanced.

7. The method of claim 1, wherein the step of rotating the rotator from the first orientation comprises rotating the rotator no more than 30° about the central axis in either direction, the drive surfaces and driven surfaces being respectively configured to cooperate and preclude the need to rotate the rotator by 30° or more in either or both directions before the rotator can be axially advanced.

8. A method of implanting and adjusting a heart valve within a human annulus comprising:

preparing the annulus for implantation of a heart valve;

providing a heart valve having an outer sewing ring and an inner rotor rotatably received within the sewing ring and including an inner wall having a plurality of discrete, inwardly facing driven surfaces;

locating the heart valve proximate the annulus;

suturing the sewing ring to the annulus;

providing a valve rotator including a proximal handle and a distal body, the body having a plurality of discrete, outwardly facing drive surfaces on a distal end, the number of drive surfaces being greater than the number of driven surfaces formed on the rotor;

positioning the distal end of the valve rotator proximate of the valve rotor;

rotating the rotator and axially advancing it to engage at least one of the drive surfaces with at least one of the driven surfaces;

wherein at least one drive surface remains disengaged; and rotating the rotor within the sewing ring.

9. The method of claim 8, wherein the drive surfaces comprise flats interrupting a annular peripheral surface, and the driven surfaces comprise flats formed on the inner wall of the rotor.

10. The method of claim 9, wherein the drive surfaces and the driven surfaces are respectively arranged in diametrically opposed flats, and there are at least three pairs of diametrically opposed flats formed on the annular peripheral surface, and the driven surfaces comprise a single pair of diametrically opposed flats.

11. The method of claim 8, further including disengaging the rotator and the rotor by axially withdrawing the rotator without any further manipulation thereof.

12. The method of claim 8, wherein the drive surfaces and the driven surfaces are respectively arranged in diametrically opposed pairs, and there are more than one pair of diametrically opposed drive surfaces on the rotator, and a single pair of diametrically opposed driven surfaces on the rotor.

13. A valve rotator adapted to be used to engage and rotate a heart valve rotor, the rotor being mounted within a frame adapted for suturing to tissue, the rotor including one or more leaflets and an inner peripheral surface having a pair of diametrically opposed driven flats formed therein, the valve rotator comprising:

a body having a proximal handle and a distal annular wall defining a central axis and terminating in an annular peripheral surface, the peripheral surface being interrupted by a plurality of discrete, outwardly facing drive flats shaped to mate with the driven flats of the rotor, the number of drive flats provided on the rotator being greater than the number of driven flats formed on the rotor, and the drive flats being arranged such that the rotator can be rotated less than 90° about the central axis in either direction and axially advanced to engage the driven flats and the driven flats.

14. The rotator of claim 13, wherein there are more than two drive flats on the annular peripheral surface.

15. The rotator of claim 14, wherein there are at least two pairs of diametrically opposed drive flats.

16. The rotator of claim 15, wherein there are three pairs of diametrically opposed drive flats.

17. A method of implanting and adjusting a heart valve in an orifice of human heart, comprising:

providing a heart valve having an outer sewing ring and an inner rotor with an inner surface having a plurality of discrete, inwardly facing driven surfaces, the rotor being rotatable with respect to the sewing ring and having a pair of leaflets pivotally mounted within the inner surface;

positioning the heart valve adjacent the orifice;

suturing the sewing ring to the orifice;

providing a valve rotator having a proximal handle attached to a distal body, the body terminating in an annular peripheral surface defining a central axis and a plurality of discrete drive surfaces adapted to engage the driven surfaces on the rotor and couple rotation of the rotator and rotor;

positioning the rotator distal body adjacent the heart valve rotor in a first orientation with the central axis aligned with the rotor axis of rotation;

rotating the rotator from the first orientation less than 60° about the central axis in either direction and axially advancing the rotator to engage the drive surfaces and the driven surfaces, the drive surfaces and driven surfaces being respectively configured to cooperate and preclude the need to rotate the rotator by 60° or more in either or both directions before the rotator can be axially advanced; and rotating the rotor within the sewing ring.

18. The method of claim 17, wherein the step of rotating the rotator from the first orientation comprises rotating the rotator no more than 30° about the central axis in either direction, the drive surfaces and driven surfaces being respectively configured to cooperate and preclude the need to rotate the rotator by 30° or more in either or both directions before the rotator can be axially advanced.

19. The method of claim 17, wherein the drive surfaces comprise outwardly facing flats interrupting the annular peripheral surface, and the driven surfaces comprise flats formed on the inner rotor surface.

20. The method of claim 19, wherein there are at least three pairs of diametrically opposed flats formed on the annular peripheral surface, and the driven surfaces comprise a single pair of diametrically opposed flats.

21. The method of claim 17, further including disengaging the rotator and the rotor by axially withdrawing the rotator without any further manipulation thereof.

22. The method of claim 17, wherein there is more than one pair of diametrically opposed drive surfaces on the rotator, and a single pair of diametrically opposed driven surfaces on the rotor.

23. A method of implanting and adjusting a heart valve in an orifice of a human heart, comprising:

providing a heart valve having an outer sewing ring and an inner rotor with an inner surface having a single pair of diametrically opposed driven flats formed thereon, the rotor being rotatable with respect to the sewing ring and having a pair of leaflets pivotally mounted within the inner surface;

positioning the heart valve adjacent the orifice;

suturing the sewing ring to the orifice;

providing a valve rotator having a proximal handle attached to a distal body, the body terminating in an annular peripheral surface defining a central axis and at least three pairs of diametrically opposed discrete, outwardly facing drive flats interrupting the annular peripheral surface adapted to engage the driven flats on the rotor and couple rotation of the rotator and rotor;

positioning the rotator distal body adjacent the heart valve rotor in a first orientation with the central axis aligned with the rotor axis of rotation;

rotating the rotator from the first orientation less than 90° about the central axis in either direction and axially advancing the rotator to engage the drive flats and the driven flats; and rotating the rotor within the sewing ring.

24. The method of claim 23, wherein the step of rotating the rotator from the first orientation comprises rotating the rotator less then 60° about the central axis in either direction.

25. The method of claim 23, wherein the step of rotating the rotator from the first orientation comprises rotating the rotator no more than 30° about the central axis in either direction.

26. A method of implanting and adjusting a heart valve in an orifice of a human heart, comprising:

providing a heart valve having an outer sewing ring and an inner rotor with an inner surface having a single pair of diametrically opposed driven surfaces, the rotor being rotatable with respect to the sewing ring and having a pair of leaflets pivotally mounted within the inner surface;

position the heart valve adjacent the orifice;

suturing the sewing ring to the orifice;

providing a valve rotator having a proximal handle attached to a distal body, the body terminating in an annular peripheral surface defining a central axis and a plurality of pairs of diametrically opposed discrete, outwardly facing drive surfaces adapted to engage the driven surfaces on the rotor and couple rotation of the rotator and rotor;

positioning the rotator distal body adjacent the heart valve motor in a first orientation with the central axis aligned with the rotor axis of rotation;

rotating the rotator from the first orientation less than 90° about the central axis in either direction and axially advancing the rotator to engage the drive surfaces and the driven surfaces; and rotating the rotor within the sewing ring.

27. The method of claim 26, wherein the step of rotating the rotator from the first orientation comprises rotating the rotator less than 60° about the central axis in either direction.

28. The method of claim 26, wherein the step of rotating the rotator from the first orientation comprises rotating the rotator no more than 3020 about the central axis in either direction.

29. A method of implanting and adjusting a heart valve in an orifice of a human heart, comprising:

providing a heart valve having an outer sewing ring and an inner rotor with an inner surface having a single pair of diametrically opposed discrete, inwardly facing driven surfaces, the rotor being rotatable with respect to the sewing ring and having a pair of leaflets pivotally mounted within the inner surface;

positioning the heart valve adjacent the orifice;

suturing the sewing ring to the orifice;

providing a valve rotator having a proximal handle attached to a distal body, the body terminating in an annular peripheral surface defining a central axis and more than one pair of diametrically opposed discrete, outwardly facing drive surfaces adapted to engage the driven surfaces on the rotor and couple rotation of the rotator and rotor;

positioning the rotator distal body adjacent the heart valve rotor in a first orientation with the central axis aligned with the rotor axis of rotation;

rotating the rotator from the first orientation less than 60° about the central axis in either direction and axially advancing the rotator to engage the drive surfaces and the driven surfaces; and rotating the rotor within the sewing ring.

30. The method of claim 29, wherein the drive surfaces comprise flats interrupting the annular peripheral surface, and the driven surfaces comprise flats formed on the inner rotor surface.

31. The method of claim 30, wherein there are at least three pairs of diametrically opposed flats formed on the annular peripheral surface, and the driven surfaces comprise a single pair of diametrically opposed flats.

* * * * *